(12) United States Patent
Shibata

(10) Patent No.: US 7,022,110 B2
(45) Date of Patent: Apr. 4, 2006

(54) NEEDLE FOR MEDICAL USE

(75) Inventor: Takeru Shibata, Kanagawa (JP)

(73) Assignee: SCITEC K.K., Kanagawa (JP)

( * ) Notice: Subject to any disclaimer, the term of this patent is extended or adjusted under 35 U.S.C. 154(b) by 0 days.

(21) Appl. No.: 10/520,370

(22) PCT Filed: Jul. 14, 2003

(86) PCT No.: PCT/JP03/08917

§ 371 (c)(1),
(2), (4) Date: Jan. 6, 2005

(87) PCT Pub. No.: WO2004/007011

PCT Pub. Date: Jan. 22, 2004

(65) Prior Publication Data

US 2005/0240152 A1 Oct. 27, 2005

(51) Int. Cl.
*A61M 5/178* (2006.01)

(52) U.S. Cl. ................ 604/158; 604/274; 604/164.01; 604/264; 606/185

(58) Field of Classification Search .......... 604/164.01, 604/158, 161, 272–274, 264, 170.01–170.03, 604/164.06, 164.13; 606/167, 170, 185
See application file for complete search history.

(56) References Cited

U.S. PATENT DOCUMENTS

| 4,811,743 | A | * | 3/1989 | Stevens | 600/585 |
| 5,125,902 | A | * | 6/1992 | Berry et al. | 604/170.03 |
| 5,507,729 | A | * | 4/1996 | Lindenberg et al. | 604/170.01 |
| 5,797,899 | A | * | 8/1998 | Tilton, Jr. | 606/1 |
| 5,807,339 | A | * | 9/1998 | Bostrom et al. | 604/164.01 |
| 5,899,891 | A | * | 5/1999 | Racz | 604/526 |
| 6,134,467 | A | * | 10/2000 | Ouchi | 604/21 |
| 6,162,221 | A | * | 12/2000 | Ouchi | 606/49 |
| 6,371,943 | B1 | * | 4/2002 | Racz et al. | 604/274 |
| 6,371,968 | B1 | * | 4/2002 | Kogasaka et al. | 606/190 |
| 6,413,245 | B1 | * | 7/2002 | Yaacobi et al. | 604/264 |
| 6,422,865 | B1 | * | 7/2002 | Fischer | 433/81 |
| 6,428,502 | B1 | * | 8/2002 | Lang | 604/28 |
| 6,478,775 | B1 | * | 11/2002 | Galt et al. | 604/158 |
| 6,497,714 | B1 | * | 12/2002 | Ishikawa et al. | 606/169 |
| 6,589,227 | B1 | * | 7/2003 | Sønderskov Klint | 604/524 |
| 6,656,160 | B1 | * | 12/2003 | Taylor et al. | 604/158 |

* cited by examiner

*Primary Examiner*—Cris Rodriguez
(74) *Attorney, Agent, or Firm*—Takeuchi&Kubotera,LLP

(57) ABSTRACT

A medical needle includes a solid rod-like inner needle to be inserted into the living tissue, and a hollow cylindrical outer tube needle to be inserted into the living tissue together with the inner needle, while the inner needle is inserted into the inner needle. The hollow cylindrical outer tube needle is retained in the living tissue after the inner needle is removed. A tip portion of the inner needle extending out of a front end bore of the outer tube needle is formed as a spherical crown portion capable of being inserted along a punctured hole previously formed in the living tissue so as not to damage the lumen of the punctured hole. Accordingly, it is possible to reduce a pain upon creating a puncture, subcutaneous bleeding and damage to a blood vessel wall, eliminate coring, and an infectious accident.

4 Claims, 6 Drawing Sheets

NEEDLE FOR MEDICAL USE

FIELD OF THE INVENTION

The present invention relates to medical treatment in a broad sense, more particularly to a medical needle comprising an inner needle which is inserted into living tissue, and a hollow cylindrical outer tube needle which is inserted into the living tissue together with the inner needle, with the inner needle being inserted thereinto, and is retained in the living tissue after the inner needle is removed; and still more particularly to a medical needle inserted into a blood vessel in the human body for use in a blood circuit during hemodialysis.

BACKGROUND

Conventionally, to extracorporeally circulate blood during hemodialysis, a method, with which two medical puncture needles of 14 to 19 gauge having a sharp tip are inserted into so-called blood accesses provided in a patient's arm for securing routes for the arterial side and for the venous side, for drawing blood out of the body through a blood circuit including these routes has been widely used.

As a medical puncture needle, that of indwelling type 1, as shown in FIG. 9, with which a tubularly formed hollow metal needle is used, being kept inserted into the human body, has long been known, however, that of outer tube-indwelling type 2 that is formed to have a dual-tube structure consisting of an outer tube needle 3 and an inner needle 4, as shown in FIG. 10, which are inserted into a blood vessel together before the inner needle 4 is removed, and then the outer tube needle 3 alone is kept inserted and retained in the blood vessel, has been in wide spread use. More recently, the medical needle of outer tube-indwelling type 5, with which an inner needle 6 is formed to be solid rather than tubular, being made of metal, as shown in FIG. 11, has also been known.

With any of said medical puncture needles of type 1, 2, 5, the tip portion of the needle (inner needle) 1, 4, 6 has been formed to be sharp so as to pierce the skin or a blood vessel of a patient, and typically the tip portion of the needle (inner needle) 1, 4, 6 has been cut off at an oblique angle with respect to the direction of the axis, as shown in FIG. 9 to FIG. 11, and provided with an edge 7 steeply sloping down toward the needlepoint thereof.

However, with conventional medical puncture needles 1, 2, 5, as described above, a thick needle of 14 to 19 gauge in diameter size is used in order to secure the blood flow rate required for hemodialysis (200 to 300 mi/mm), and thus there is a problem that the patient is forced to endure the pains involved in creating a puncture (boring pains) at every dialysis session carried out two or three times a week, for example.

Further, the tip portion of the needle (inner needle) 1, 4, 6 has a sharp edge 7 sloping down toward the needlepoint in order to facilitate the insertion into the skin and a blood vessel wall, as described above, thus there has been a possibility that, if the thick hollow needle 1, 4 is used, so-called coring may occur at the time of puncture, causing a part of the living tissue in the skin or a blood vessel to be scraped off into the hollow needle 1, 4 and flow into the blood vessel. Further, because the tip is sharp, a mere touch with the needle has tended to cause wrong puncture, and thus puncture troubles due to such wrong puncture, such as subcutaneous bleeding, could not have been effectively avoided, giving patients pain.

Further, the repetition of puncturing scrapes off and thus damages the tissue at the puncture site in the so-called blood accesses, hardens the living tissue, and forms swelling, leading to reduction in the service life of the blood accesses. Still further, there has been a problem that, when a blood access formed with an artificial blood vessel is punctured, puncturing in the same part must be avoided because an artificial blood vessel is slow to recover from the damage given to it at a puncture site, and thus many holes have been made in the patient's blood vessel every time dialysis is carried out, forcing the patient to endure further pains.

Further, although a needle which has been removed from a patient is subjected to disposal, a health-care worker might accidentally touch the sharp needlepoint thereof, getting injured, resulting in an infection accident, thus the necessity of eliminating such problem has been presented.

Being developed in consideration of the problems of the prior arts as described above, the purpose of the present invention is to provide a medical needle which can greatly reduce the pains involved in creating a puncture, avoid subcutaneous bleeding and damage to blood vessel walls by preventing wrong puncture, eliminate the possibility that coring may occur, causing further damage to the living tissue and a part of the living tissue to flow into a blood vessel, and prevent infection accidents due to wrong puncture, thus assuring a high level of safety of health-care workers.

SUMMARY OF THE INVENTION

According to the present invention there is provided a medical needle, comprising an inner needle which is inserted into living tissue, and a hollow cylindrical outer tube needle which is inserted into the living tissue together with the inner needle, with the inner needle being inserted thereinto, and is retained in the living tissue after the inner needle is removed, wherein the tip portion of the inner needle extending out of the front end bore of said outer tube needle is formed as a spherical crown portion which is capable of being inserted along a punctured hole previously formed in the living tissue so as not to damage the lumen of the punctured hole, and said inner needle comprises:

a main body portion which is formed to have an outside diameter which is approximately equal to the inside diameter of said outer tube needle;

a tapered portion which integrally connects to the front end portion of the main body portion, extends along the axis of the main body portion, being gradually decreased in diameter, and extends out of the front end bore of said outer tube needle; and a small-diameter portion which further extends a prescribed length from the front end portion of the tapered portion along said axis, having a diameter which is approximately equal to the smallest diameter of the front end portion thereof, and the tip portion of the small-diameter portion is formed as said spherical crown portion.

With the medical needle according to the present invention, the tip portion of the inner needle is formed as a spherical crown portion, and by inserting this spherical crown portion into the punctured hole previously formed in the living tissue the medical needle can be smoothly inserted into the living tissue while widening out the punctured hole without causing damage to the lumen thereof, thus eliminating the pains which would be involved in creating a new puncture. Further, there is no possibility that coring may occur, causing further damage to the living tissue and a part of the living tissue to flow into a blood vessel.

Because the tip portion of said inner needle is formed as a spherical crown portion, and the omnidirectionally spherical surface thereof comes into smooth contact with the living tissue, it will not puncture the living tissue as long as it is merely contacted with or lightly pressed against the living tissue. Thereby, wrong puncture to the patient herself/himself can be prevented; subcutaneous bleeding and damage to blood vessel walls can be avoided; wrong puncture to health-care workers can also be avoided; and infection accidents can be prevented, thus a high level of safety can be assured.

When the medical needle is used, the inner needle is inserted into the outer tube needle to be an integral part, and as the inner needle is inserted into a punctured hole previously formed in the living tissue from the spherical crown portion provided at the tip thereof, as described above, the outer tube needle is also inserted into the blood vessel, passing through the punctured hole, together with the inner needle. Thereafter, the outer tube needle is retained as it is, and the inner needle alone is removed from the outer tube needle for allowing the outer tube needle to be used as a flow passage for a blood circuit. Said inner needle may be formed in a solid rod-like shape over the entire length thereof, or said inner needle may be formed to have a through hole substantially passing through the axis over the entire length thereof.

More particularly, the inner needle may be configured to comprise a main body portion which is formed to have an outside diameter which is approximately equal to the inside diameter of the outer tube needle; a tapered portion which integrally connects to the front end portion of the main body portion and extends along the axis of the main body portion, while being gradually decreased in diameter and extends out of the front end bore of said outer tube needle; and a small-diameter portion which further extends a prescribed length from the front end portion of the tapered portion along said axis, having a diameter which is approximately equal to the smallest diameter of the tapered portion at the front end thereof, the tip portion of the small-diameter portion being formed as a spherical crown portion.

Thereby, for a while after the spherical crown portion is first inserted into the punctured hole, the small-diameter portion passes through the punctured hole, and therefore the punctured hole is given time to adjust itself to the expansion rather than being abruptly subjected to great expansion, and then gradually expanded by the tapered portion. Especially, even when it is required to search for the punctured hole in the blood vessel wall due to a slight dislocation thereof after the insertion and passing through the punctured hole in the skin and subcutaneous tissue, slightly moving the entire needle, while passing through the subcutaneous tissue, will not greatly expand the punctured hole because the portion passed through the subcutaneous tissue is a small-diameter portion.

Further, because the tip portion of the inner needle is formed as a spherical crown portion, and the omnidirectionally spherical surface thereof comes into smooth contact with the living tissue, as described above, the surface of the blood vessel wall will not undesirably be damaged even when it is lightly rubbed with the spherical crown portion in searching for the location of the punctured hole in the surface of the blood vessel wall. Therefore, the front end portion of the inner needle can be smoothly inserted into the punctured hole and connected to the interior of the blood vessel, with practically no pains being given to the patient, and then the tip bore portion of the outer tube needle can also be smoothly inserted into the blood vessel, together with the main body portion of the inner needle, along the punctured hole. Further, even when the inner needle is removed, it can be smoothly withdrawn with practically no pains being given to the patient.

If the diameter of the spherical crown portion is adapted to be still larger than the outside diameter of said small-diameter portion, the spherical surface of the spherical crown portion can be brought into contact with the living tissue over a wider angular range, and the small-diameter portion can advance more smoothly after the spherical crown portion is inserted into the punctured hole. Further, if the diameter of the spherical crown portion is adapted to be approximately equal to the outside diameter of said small-diameter portion, the spherical crown portion can be more smoothly inserted into the punctured hole at the beginning of the insertion of the inner needle.

BEST MODES FOR CARRYING OUT THE INVENTION

Hereinbelow, exemplary embodiments of the present invention will be described with reference to the drawings.

FIG. 1 to FIG. 5 show a first embodiment of the present invention.

Figure 1:
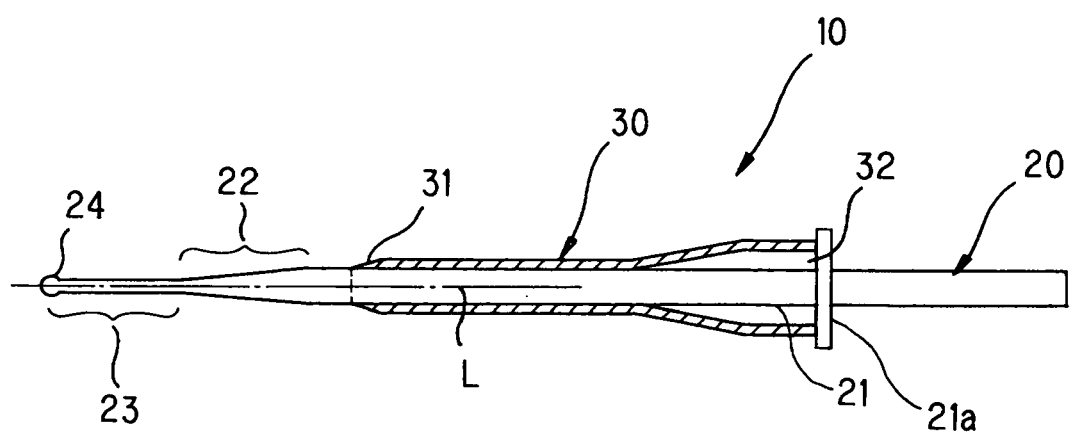
FIG. 1 is a partially sectional view illustrating a medical needle according to a first embodiment of the present invention.

As shown in FIG. 1, a medical needle 10 is used by inserting an inner needle 20 into an outer tube needle 30 with integrally combining them with each other. Herein, an application where the medical needle 10 is connected to each of the blood accesses for the arterial side and for the venous side in a patient's arm during hemodialysis will be used for description.

Figure 3:
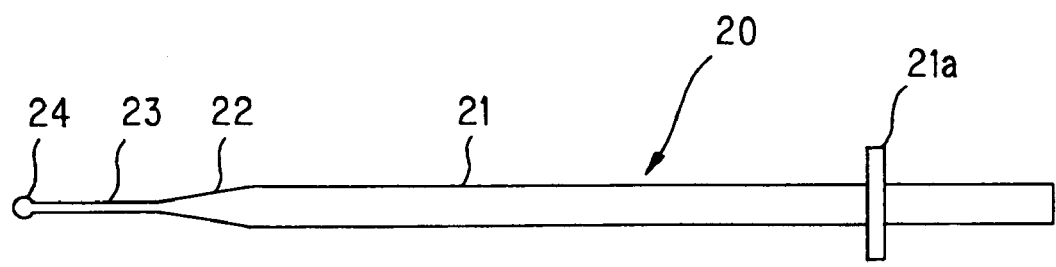
FIG. 3 is a front view illustrating an inner needle constituting the medical needle according to the first embodiment of the present invention.

As shown in FIG. 3, the inner needle 20 is a solid rod-like needle made of a metal such as stainless steel or titanium, for example, and provides a portion which, in using the medical needle 10, is first inserted into a punctured hole which was once formed in a patient's arm. The word "solid rod-like" used here means that the inner needle 20 is not structured as a tubular rod, which has a space inside it, but as a solid rod, having no space inside it. In addition, the term "rod-like" is used as opposed to the term "tubular," and it is needless to say that the term is intended to provide a concept of thin article like an ordinary needle.

More particularly, the inner needle 20 comprises a main body portion 21 which is formed to have an outside diameter which is approximately equal to the inside diameter of an outer tube needle 30 later described; a tapered portion 22 which integrally connects to the front end portion of the main body portion 21 and extends along the axis L of the main body portion 21, while being gradually decreased in diameter; and a small-diameter portion 23 which further extends a prescribed length from the front end portion of the tapered portion 22 along said axis L, having a diameter which is approximately equal to the smallest diameter of the tapered portion 22 at the front end thereof.

The outside diameter of the main body portion 21 is practically uniform and formed slightly smaller than the inside diameter of the critical portion of the outer tube needle 30 later described. The main body portion 21 is slidable relative to the inner surface of the outer tube needle 30, but, the fitting between both may be set such that the outer tube needle 30 is held, being externally fitted to the inner needle 20, and not easily displaced or comes off unless subjected to a force from the outside.

The main body portion 21 on the basal end side further extends out of the basal end bore 32 in the outer tube needle 30, and, at the midpoint of extension, a grip portion 21a in the shape of a flange is integrally provided. The actual length of the main body portion 21 may be 93.5 to 103.5 mm, for example, in consideration of the typical overall length of the inner needle 20 (for example, 100 to 110 mm). The actual outside diameter of the main body portion 21 may be 1.25 mm (18 G) or 1.05 mm (19 G), for example.

The tapered portion 22 is a substantially cone-shaped portion which is integrally connected to the front end portion of said main body portion 21 extending out of the front end bore 31 in the outer tube needle 30 and extends along the axis L of the main body portion 21, while being gradually decreased in diameter. The entire tapered portion 22 is set to be completely exposed, extending out of the front end bore 31 in the outer tube needle 30. Specifically, the actual length of the tapered portion 22 may be 2.5 mm or so, for example.

The small-diameter portion 23 is a portion which further extends a prescribed length from the front end portion of said tapered portion 22 along said axis L, having a diameter which is approximately equal to the smallest diameter of the tapered portion 22 at the front end thereof. Specifically, the actual length of the small-diameter portion 23 may be 4.0 mm or so, for example, in consideration of the typical distance from the skin to a blood vessel wall when the medical needle 10 is inserted into the living tissue at a prescribed oblique angle. The actual outside diameter of the small-diameter portion 23 may be 0.72 mm (22 G) or so, for example.

Figure 2:
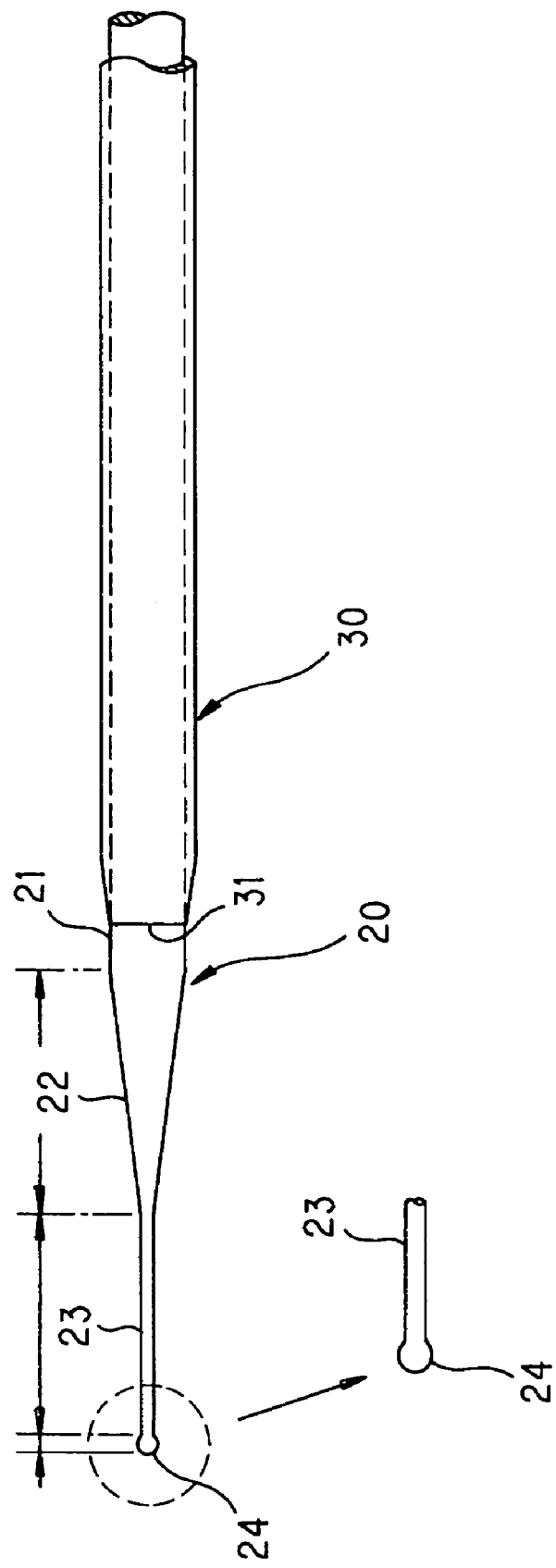
FIG. 2 is a critical portion enlarged view illustrating the medical needle according to the first embodiment of the present invention.

As shown in FIG. 2, the tip portion of the small-diameter portion 23, that is, the tip portion of the inner needle 20 is formed as a spherical crown portion 24. The spherical crown portion 24 is a portion which is formed in the shape of a sphere, except for a portion which connects to the front end portion of said small-diameter portion 23, and with such shape, the spherical crown portion 24 can be inserted along the punctured hole previously formed in the living tissue so as not to damage the lumen of the punctured hole. In the present embodiment, the diameter of the spherical crown portion 24 is adapted to be slightly larger than the outside diameter of said small-diameter portion 23, and specifically it may be 0.9 to 1.0 mm, for example.

Figure 4:
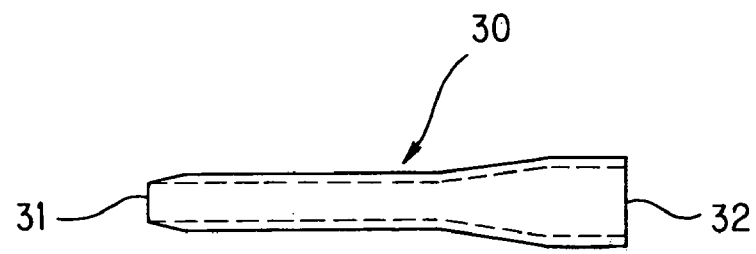
FIG. 4 is a front view illustrating an outer tube needle constituting the medical needle according to the first embodiment of the present invention.

As shown in FIG. 4, the outer tube needle 30 is a hollow cylindrical tube and is a portion which is inserted into the living tissue together with the inner needle 20, while being externally fitted to said inner needle 20, and then retained in the living tissue after the inner needle 20 alone being removed. The outer tube needle 30 may be made of a soft resin such as flexible Teflon (registered trademark) in order to be able to follow the movement of a human body to a certain degree, and not to damage blood vessels, because it is retained, being connected to the interior of a blood vessel during hemodialysis.

The front end bore 31 of the outer tube needle 30 is adapted to be positioned in the front end portion of the main body portion 21 of the inner needle 20 when it is externally fitted to the inner needle 20, and the outer surface of the front end bore 31 is tapered in order to reduce the resistance during insertion through said punctured hole. The basal end portion of the outer tube needle 30 is formed thick, compared with the front end portion, and the basal end bore 32 is adapted to be connected to the end portion of a blood circuit (not shown in figures).

Next, the function of the medical needle 10 according to the first embodiment will be described.

Figure 9:
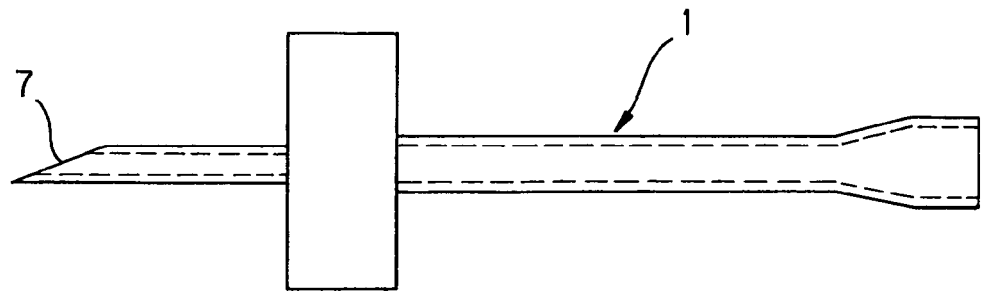
FIG. 9 is a front view illustrating a conventional medical needle.
Figure 10:
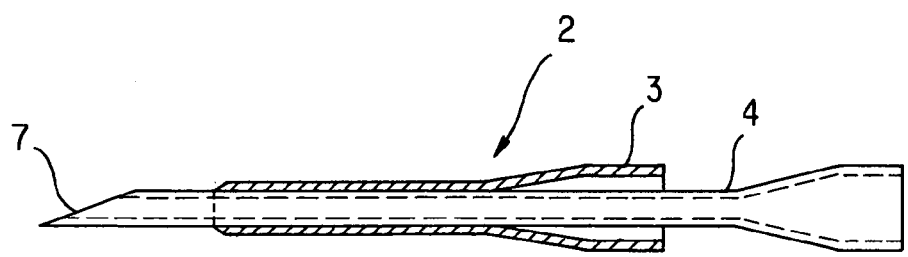
FIG. 10 is a front view illustrating another conventional medical needle.
Figure 11:
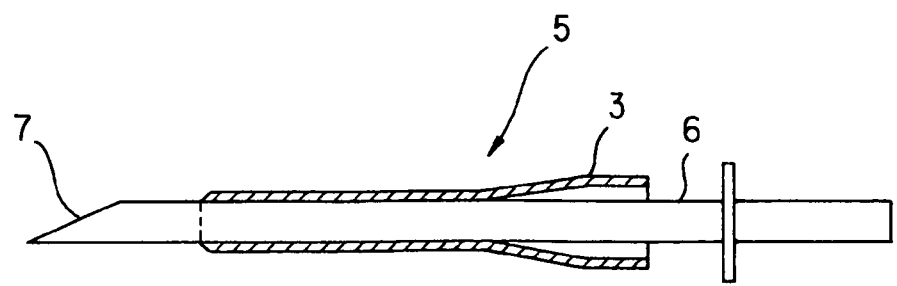
FIG. 11 is a front view illustrating a still another conventional medical needle.

When hemodialysis is carried out, a puncture route is first created in the blood access in a patient's arm, using an ordinary puncture needle (see FIG. 9 to FIG. 11) similar to the conventional needle, at a first dialysis session. Then, said medical needle 10 is used at the second and subsequent dialysis sessions. When the medical needle 10 is used, the inner needle 20 is first inserted into and integrally combined with the outer tube needle 30, as shown in FIG. 1.

The tip portion of the inner needle 20 which provides the front end portion of the medical needle 10 is formed as a spherical crown portion 24, and by inserting this spherical crown portion 24 into the punctured hole previously formed at said first dialysis session, the medical needle 10 can be smoothly inserted into the living tissue while widening out the punctured hole without causing damage to the lumen thereof, thus eliminating the pains which would be involved in creating a new puncture. Further, there is no possibility that coring may occur, causing further damage to the living tissue and a part of the living tissue to flow into a blood vessel.

Figure 5:
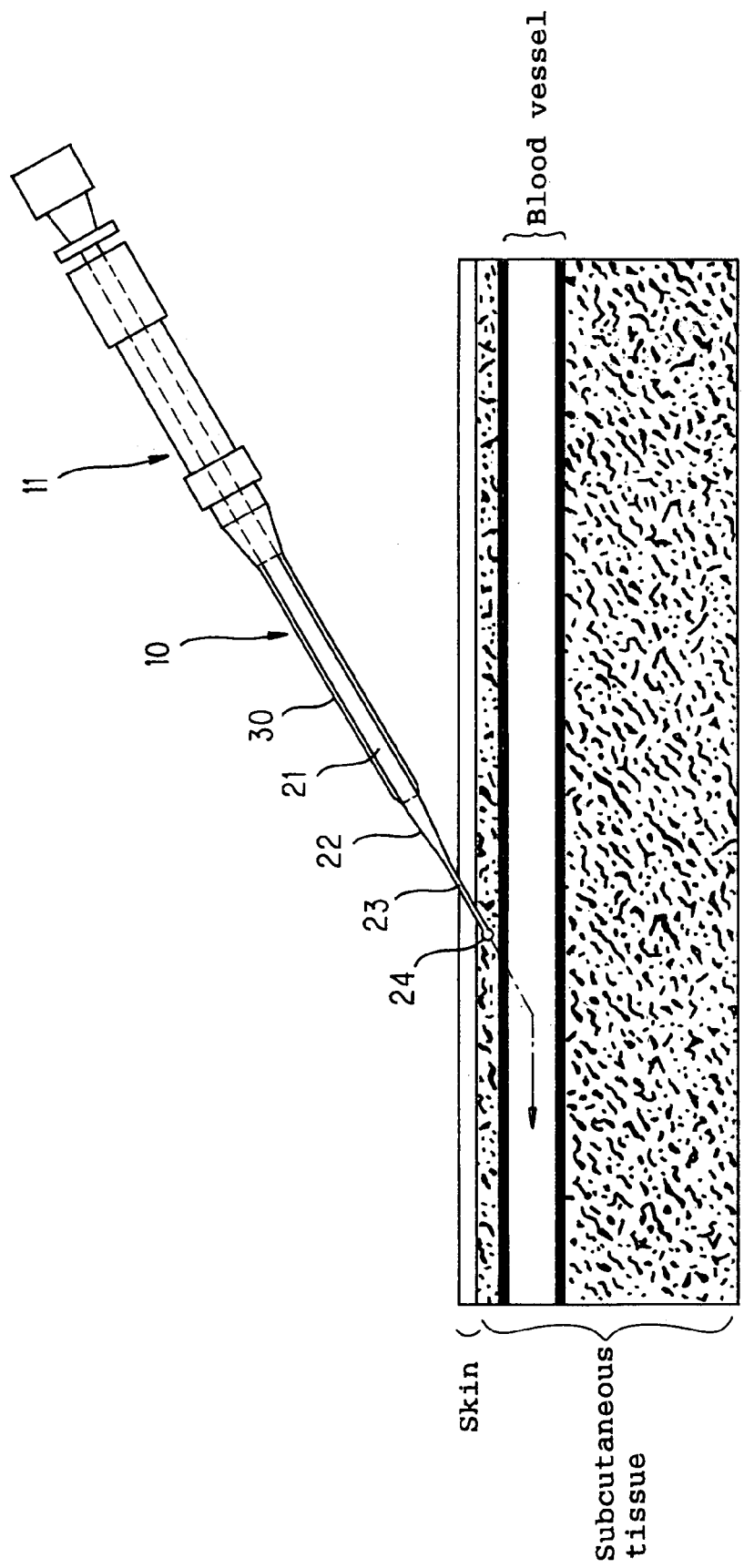
FIG. 5 is an explanatory view illustrating the function of the medical needle according to the first embodiment of the present invention.

Particularly, as shown in FIG. 5, the medical needle 10 is applied to the patient's arm at a prescribed oblique angle, and the tip portion thereof, i.e., the spherical crown portion 24 of the inner needle 20 is slowly inserted from the inlet of the punctured hole previously formed in the skin. The medical needle 10 is used while being attached to a special casing 11. Until the spherical crown portion 24 reaches a blood vessel after the spherical crown portion 24 is first inserted into the punctured hole, the small-diameter portion 23 passes through the punctured hole left in the subcutaneous tissue, following the spherical crown portion 24, and therefore the punctured hole is given time to adjust itself to the expansion rather than being abruptly subjected to great expansion, and then gradually expanded by the tapered portion 22.

Even when it is required to search for the punctured hole in the blood vessel wall due to a slight dislocation thereof after the spherical crown portion 24 or the entire small-diameter portion 23 being inserted into and passed through the punctured hole in the skin and subcutaneous tissue, slightly moving the entire needle will not greatly expand the punctured hole because the portion passed through the subcutaneous tissue is a small-diameter portion 23. The omnidirectionally spherical surface of the spherical crown portion 24 comes into smooth contact with the living tissue, as described above, thus the surface of the blood vessel wall will not undesirably be damaged even when it is lightly rubbed with the spherical crown portion 24 to search for the location of the punctured hole in the surface of the blood vessel wall.

Therefore, when the medical needle 10 is inserted into the blood vessel at the second and subsequent dialysis sessions, the front end portion of the inner needle 20 can be smoothly inserted into the punctured hole and connected to the interior of the blood vessel, with practically no pains being given to the patient. When the medical needle 10 is inserted, the front end bore 31 of the outer tube needle 30 is positioned in the front end portion of the main body portion 21 of the inner needle 20, being tightly contacted therewith, and the outer surface of the main body portion 21 is tapered, thus the outer tube needle 30 is also smoothly inserted into the blood vessel, together with the inner needle 20, through the punctured hole, without the front end bore 31 of the outer tube needle 30 being caught in the lumen of the punctured hole.

Therefore, the patient hardly feels any pain even when the outer tube needle 30 is inserted, following the inner needle 20. Thereafter, the outer tube needle 30 is retained as it is, while being connected to the interior of the blood vessel, and the inner needle 20 alone is removed from the outer tube needle 30, which allows the outer tube needle 30 to be used as a flow passage for the blood circuit. Even when the inner needle 20 is removed, it can be smoothly withdrawn with practically no pains being given to the patient, and there is no possibility that the needlepoint thereof may damage or break the inner surface of the outer tube needle 30, which is made of a soft resin such as Teflon (registered trademark).

Because the tip portion of the inner needle 20 is a spherical crown portion 24, and the omnidirectionally spherical surface thereof comes into smooth contact with the living tissue, it will not puncture the living tissue as long as it is merely contacted with or lightly pressed against the living tissue. Thereby, wrong puncture to the patient herself/himself can be prevented; subcutaneous bleeding and damage to blood vessel walls can be avoided; wrong puncture to health-care workers can also be avoided; and infection accidents can be prevented, thus a high level of safety can be assured.

Figure 6:
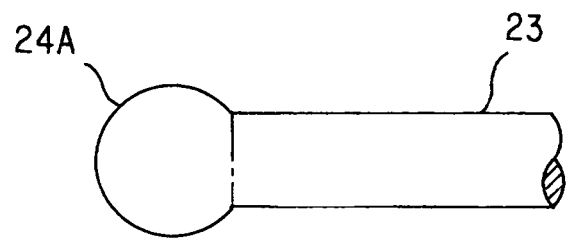
FIG. 6 is a critical portion enlarged view illustrating a medical needle according to a second embodiment of the present invention.

FIG. 6 shows a second embodiment of the present invention.

In the second embodiment, the diameter of the spherical crown portion 24A is adapted to be still larger than the outside diameter of the spherical crown portion 24 according to said first embodiment. Specifically, the diameter of the spherical crown portion 24A may be 1.2 to 1.3 mm, for example, while the outside diameter of a small-diameter portion 23 is 0.72 mm (22 G).

Thereby, the spherical surface of the spherical crown portion 24A can be brought into contact with the living tissue over a wider angular range, and the small-diameter portion 23 can advance more smoothly after the spherical crown portion 24A is inserted into the punctured hole. The portions similar to those of the first embodiment are provided with the same reference signs to avoid duplication of the explanations.

Figure 7:
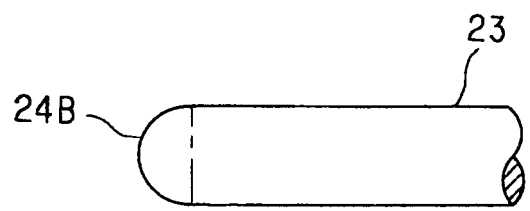
FIG. 7 is a critical portion enlarged view illustrating a medical needle according to a third embodiment of the present invention.

FIG. 7 shows a third embodiment of the present invention.

In the third embodiment, the diameter of the spherical crown portion 24B is adapted to be approximately equal to the outside diameter of said small-diameter portion 23, and the diameter of the spherical crown portion 24B may be 0.72 mm, for example, while the outside diameter of the small-diameter portion 23 is 0.72 mm (22 G).

Thereby, in the third embodiment, the spherical crown portion 24B can be easily machined, which allows cost reduction, and the spherical crown portion 24B can be more smoothly inserted into the punctured hole. The portions similar to those of the first embodiment are provided with the same reference signs to avoid duplication of the explanations.

Figure 8:
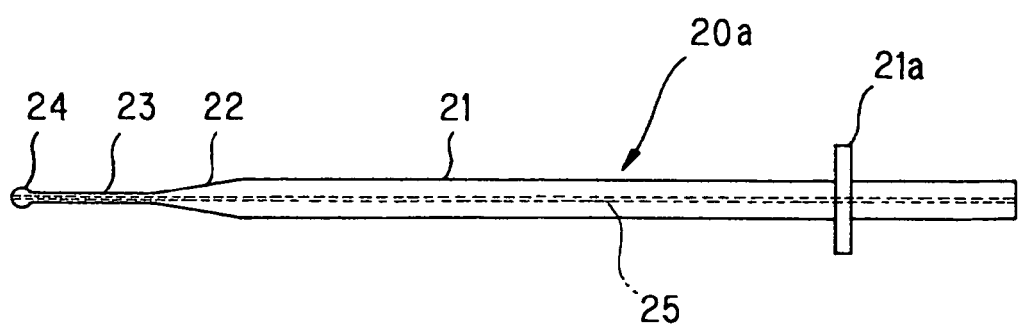
FIG. 8 is a front view illustrating an inner needle constituting a medical needle according to a fourth embodiment of the present invention.

FIG. 8 shows a fourth embodiment of the present invention.

In the fourth embodiment, said inner needle 20a is provided with a through hole 25 which substantially passes through the axis over the entire length thereof. The through hole 25 has a very fine cross sectional geometry, extending from the basal end surface of the main body portion 21, substantially passing through the axis of the inner needle 20a, and being opened at the center of the tip portion of the spherical crown portion 24.

Thereby, in the fourth embodiment, because blood flows back through the through hole 25, once the spherical crown portion 24 of the inner needle 20a reaches the interior of a blood vessel through the punctured hole, as described above, the fact that the spherical crown portion 24 has reached the interior of the blood vessel can be easily and surely confirmed by visual checking of the back-flow of the blood.

Although the embodiments of the present invention have been described with reference to the drawings, it should be noted that specific configuration is not limited to those as described in the above embodiments, and any modification or addition within the scope of the spirit of the present invention is included in the present invention.

INDUSTRIAL APPLICABILITY

With the medical needle according to the present invention, the tip portion of the inner needle inserted into and passed through the outer tube needle is formed as a spherical crown portion, and by inserting this spherical crown portion into the punctured hole previously formed in the living tissue, the medical needle can be smoothly inserted into the living tissue while widening out the punctured hole without causing damage to the lumen thereof, thus eliminating the pains which would be involved in creating a new puncture. Further, there is no possibility that coring may occur, causing further damage to the living tissue and a part of the living tissue to flow into a blood vessel.

In particular, because the omnidirectionally spherical surface of said spherical crown portion comes into smooth contact with the living tissue, it will not puncture the living tissue as long as it is merely contacted with or lightly pressed against the living tissue. Thereby, wrong puncture to the patient herself/himself can be prevented; subcutaneous bleeding and damage to blood vessel walls can be avoided; wrong puncture to health-care workers can also be avoided; and infection accidents can be prevented, thus a high level of safety can be assured.

What is claimed is:

1. A medical needle, comprising:
an inner needle to be inserted into living tissue, and
a hollow cylindrical outer tube needle to be inserted into the living tissue together with the inner needle, with the inner needle being inserted thereinto, and to be retained in the living tissue after the inner needle is removed, wherein said inner needle includes a tip portion extending out of a front end bore of said outer tube needle and having a spherical crown portion capable of being inserted along a punctured hole previously formed in the living tissue so as not to damage lumen of the punctured hole, and said inner needle further includes:

a main body portion having an outside diameter approximately equal to an inside diameter of said outer tube needle;

a tapered portion integrally connected to a front end portion of the main body portion, extending along an axis of the main body portion, and having a diameter gradually decreasing to protrude from the front end bore of said outer tube needle; and a small-diameter portion extending by a prescribed length from a front end portion of the tapered portion along said axis, and having a diameter approximately equal to a smallest diameter of a front end portion of the tapered portion, and the spherical crown portion.

2. The medical needle according to claim 1, wherein said inner needle is formed in a solid rod shape over an entire length thereof.

3. The medical needle according to claim 1, wherein said inner needle is provided with a through hole which substantially passes through the axis over an entire length thereof.

4. The medical needle according to claim 1, wherein said spherical crown portion has a diameter larger than an outside diameter of said small-diameter portion.

* * * * *